United States Patent [19]

Hammann

[11] Patent Number: 4,772,558

[45] Date of Patent: Sep. 20, 1988

[54] BLOOD CULTURE SYSTEM

[76] Inventor: Ranier Hammann, Heinbuckel 18, D-6901 Wiesenbach, Rine-Neckar-District, Baden-Wurttemberg, Fed. Rep. of Germany

[21] Appl. No.: 56,517

[22] Filed: Jun. 1, 1987

[51] Int. Cl.⁴ .............................................. C12M 1/18
[52] U.S. Cl. ...................................... 435/300; 215/6; 215/247; 220/22
[58] Field of Search .................... 435/300, 301; 215/6, 215/247; 220/22, 20.5

[56] References Cited

U.S. PATENT DOCUMENTS

| 793,327 | 6/1905 | Swoyer et al. | 215/6 |
| 2,135,386 | 11/1938 | Crabbe | 215/247 |
| 2,661,870 | 12/1953 | Huenergardt | 220/22 |
| 2,661,871 | 12/1953 | Huenergardt | 220/22 |
| 3,073,750 | 1/1963 | Greenblatt | 435/301 |

FOREIGN PATENT DOCUMENTS 3136251 4/1983 Fed. Rep. of Germany ...... 435/300

Primary Examiner—Carroll B. Dority, Jr.
Attorney, Agent, or Firm—Mary M. Allen

[57] ABSTRACT

A culture bottle assembly for the detection of microorganisms in a fluid sample is provided. The culture bottle assembly is a container having a dividing wall which divides the culture into two compartments. A cap is provided for the container and means are provided for moving the cap axially with respect to the container. A resilient material is provided which is compressed by the cap moving means to provide a liquid tight seal between the two compartments.

8 Claims, 6 Drawing Sheets

BLOOD CULTURE SYSTEM

BACKGROUND OF THE INVENTION

1. Field of the Invention

The present invention reltates to the detection of microorganisms in a fluid smaple such as, for example, body fluids. More particularly, the present invention relates to a culture bottle assembly a luqiid nutrient medium is provided in combination with a solid medium and wherein a fluid sample is incubated in the liquid nutrient medium which is then used to inoculate the solid medium and to continue the growth of organisms which are initially grown in the liquid nutrient medium.

2. Prior Art

The detection of micro-organisms in body fluids, particularly bacteria in blood, requires that a sample of the fluid be used to inoculate a liquid nutrient medium. Subsequently, the liquid medium is in turn used to inoculate a solid medium to continue the growth of the organisms and to make them visible to the naked eye as colonies.

Normal monophasic systems consist of a liquid medium in a culture bottle or vial which is inoculated with a sample of the fluid and is then incubated for a desired period of time (24–48 hours). After that, a sample is withdrawn from the bottle and is used to inoculate a solid nutrient medium (agar in a Petri dish).

This procedure is laborious, sometimes hazardous and includes the risk of contamination with microorganisms from the environment. Therefore detection systems have been developed in which liquid and solid culture media are combined in the same container. Such systems avoid the troublesome and sometimes hazardous transfer of the liquid culture to the solid culture medium. U.S. Pat. No. 2,992,974 to Belcove et al, for example, describes a biological testing device in which a solid medium is restrained in the top portion of a rectangular culture bottle while a liquid nutrient medium is provided in the lower most portion of the bottle. U.S. Pat. No. 3,589,983 to Holderith et al describes a culture bottle which is designed to hold a solid agar nutrient material at a location along the axial centerline of a bottle. The bottle also houses a liquid nutrient broth which may be separated from the solid agar by positioning the bottle on its side.

Of course, the above described prior art devices which combine a liquid nutrient medium in a single container with a solid medium have a major disadvantage in that the culture assembly must be positioned in a certain manner prior to contacting the solid medium with the precultured liquid medium. The above described prior art devices for separating solid and liquid culture media are complicated and facilitate separation of the liquid media and the solid media only during incubation, but not during transport.

U.S. Pat. No. 4,308,347 to Forrer et al describes a device for detection of microorganisms in a fluid sample which includes a first container holding a liquid nutrient medium and a second container containing one or more solid nutrient medium. The containers are detachably connected so that the media can be brought into contact when desired. The device described in the Forrer Patent is complicated and requires several manipulative steps to bring the precultured liquid media into contact with the solid medium.

The above disadvantages of the prior art are overcome in accordance with the present invention which provides a simple culture bottle assembly which contains a liquid media and one or more solid nutrient media in a single container with easily effected means for bringing the precultured liquid media into contact with the solid media when desired.

SUMMARY OF THE INVENTION

In accordance with the present invention, a device for the detection of microorganisms in body fluids is provided which is extremely simple and which avoids the disadvantages of the prior art. The culture bottle assembly of the present invention consists of a single container divided into two sections by a dividing wall. Closure means are provided which have a resilient surface tomate with the top portion of the dividing wall to close the container and to provide two sealed compartments. One of the compartments contains a liquid nutrient media and the other compartment contains one or more solid medium. After a sample is incubated in the liquid media for a desired period of time the closure means are moved to a second position which provides an opening space above the wall through which the precultured liquid media can be transferred into contact with the solid media when the container is turned over.

Further details and features of the invention will become more apparent from the following detailed description and the drawings which disclose what is presently considered to be the best mode of the invention.

THE DRAWINGS

DETAILED DESCRIPTION OF THE INVENTION

Figure 1:
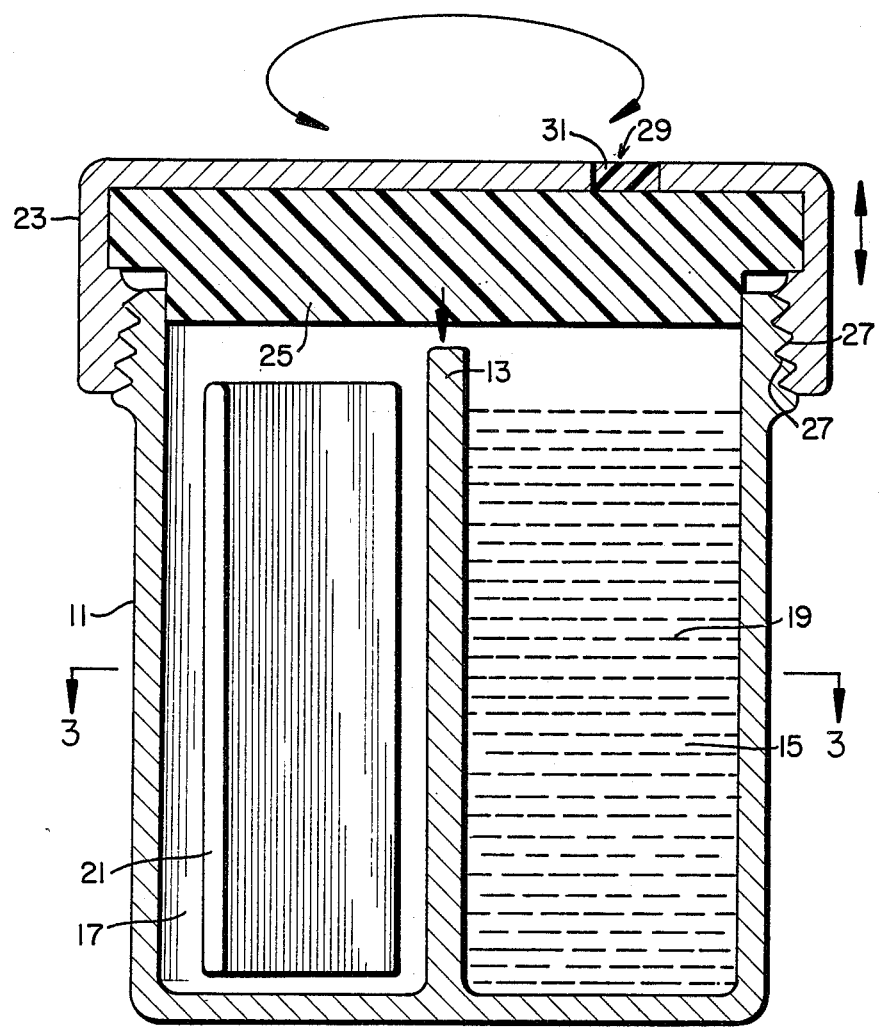
FIG. 1 is a longitudinal cross section of the container in accordance with the present invention which shows the relative location of the liquid nutrient medium and the solid medium.
Figure 2:
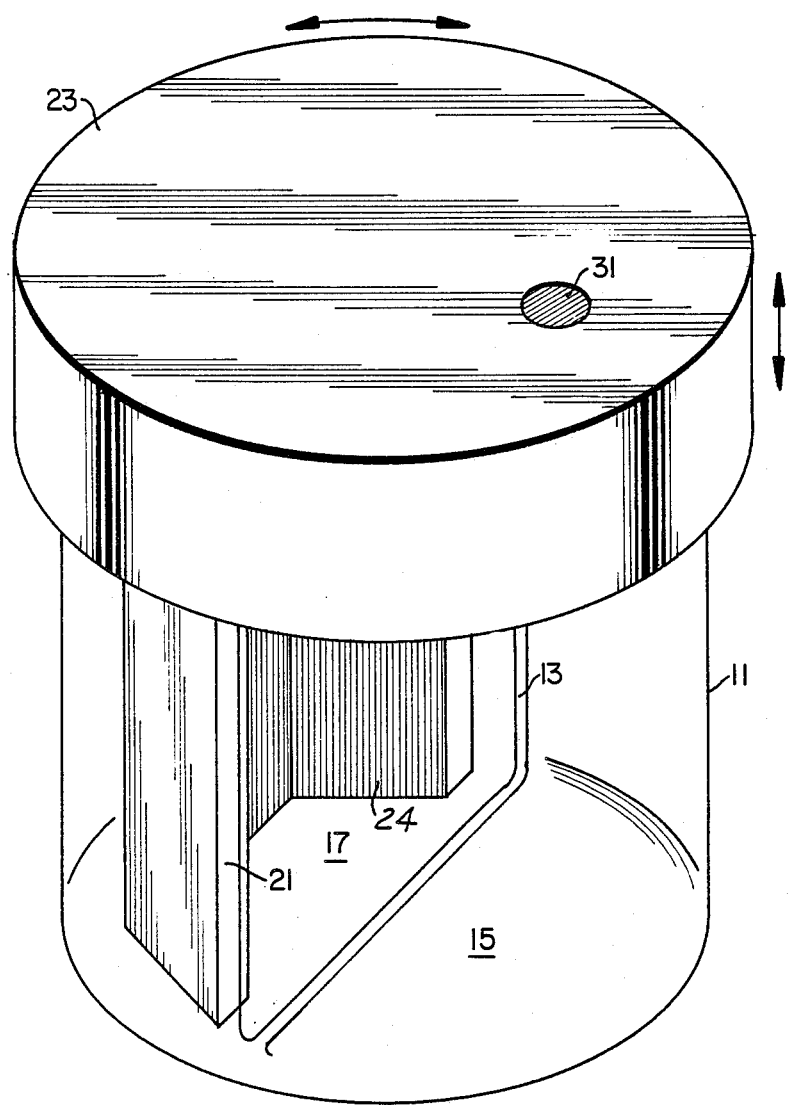
FIG. 2 is perspective view of the culture bottle assembly of the invention.
Figure 3:
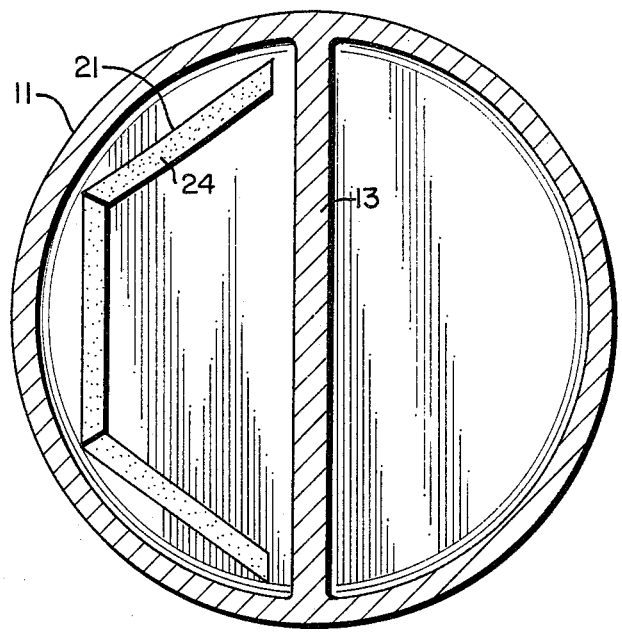
FIG. 3 is a cross sectional view of the culture bottle assembly of FIG. 2 showing a tripartite solid media assembly.
Figure 4:
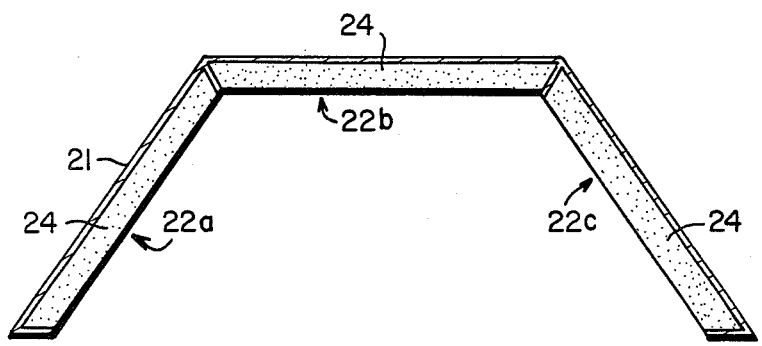
FIG. 4 is an enlarged cross section view of the tripartite solid medium tray.

Referring now to the drawings:

The container 11 is divided into a first compartment 15 and a second compartment 17 by means of a dividing wall 13. A liquid medium 19 is filled into the first compartment 15. A solid medium is dispersed onto a suitable frame 21. As shown in FIG. 2 and FIG. 4, the frame consists of 3 joined trays which provides an easy means for holding the frame upright within the container.

Figure 5:
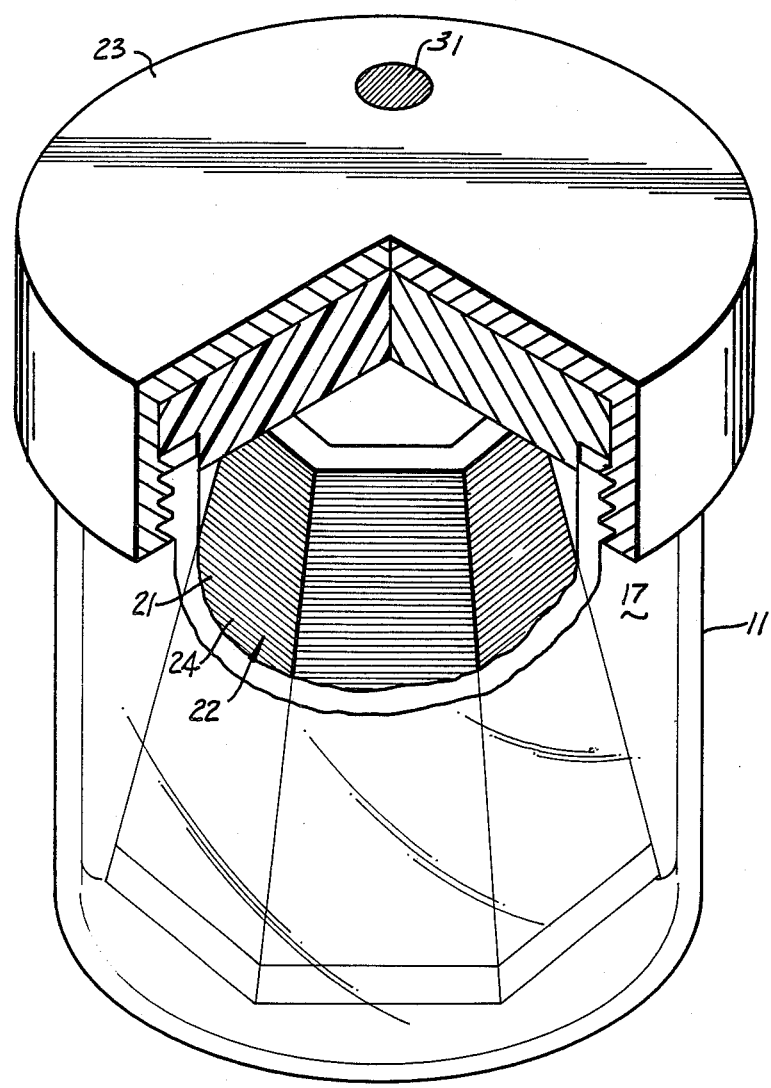
FIG. 5 is a perspective view of a further embodiment of the culture bottle assembly of the invention.
Figure 6:
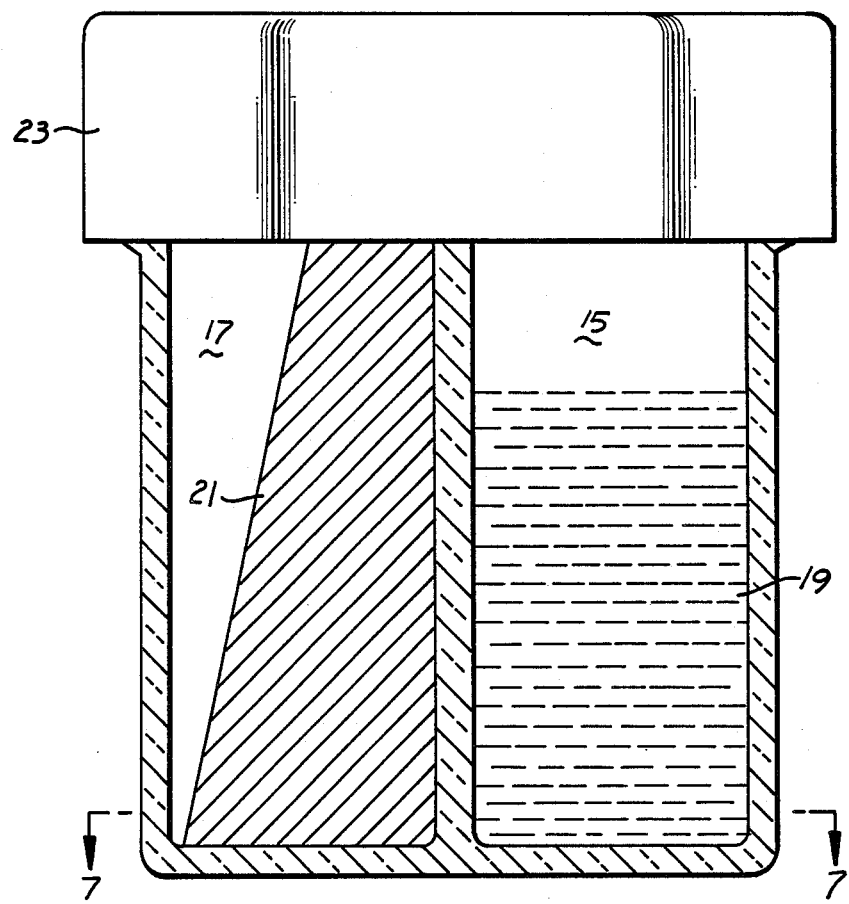
FIG. 6 is a longitudinal cross sectional view of the culture bottle assembly of FIG. 5.
Figure 7:
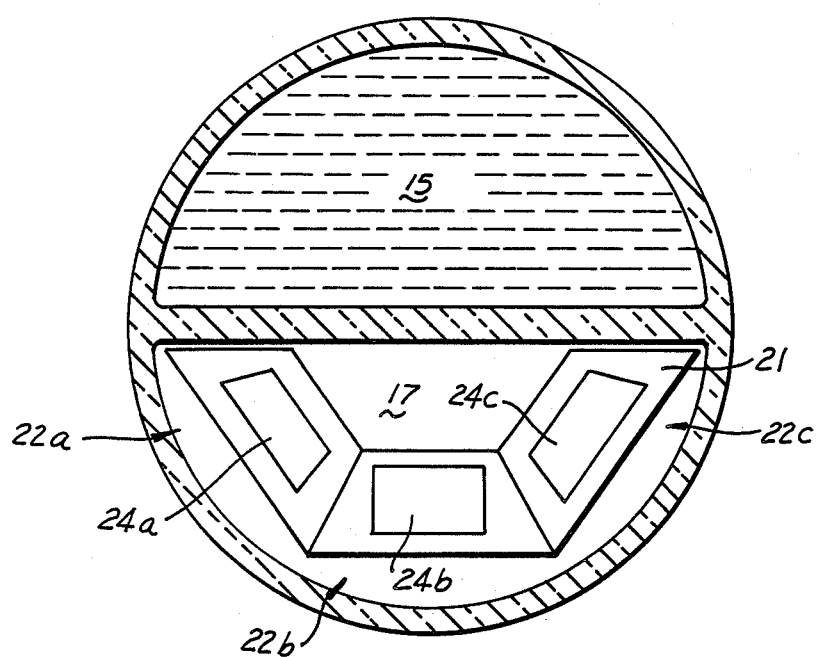
FIG. 7 is a cross sectional view of the culture bottle assembly of FIG. 6 taken along the line 7—7.

The solid medium frame 21 comprises a series of three trays 22a, 22b and 22c. In the embodiment shown in FIGS. 5–7, the frame 21 has a pyramidal shape so that the lower part of it (near the bottom of the container) is closer to the outer wall of the container than the upper part of it (near the cap). With this frame configuration, colonies of microorganisms growing on the agar in frame 21 can be picked up for further examination by means of an inoculating loop without the risk of touching the inner wall of the container. The frame 21 is made ready for use by first dispensing an agar nutrient material 24 in liquid form at an elevated temperature into the tray sections of the frame. The agar nutrient material may be the same or different in each tray. The agar is allowed to cool and solidify before the tray is inserted into the second compartment 17 of the container. A liquid medium is inserted into the first compartment 15 of the container.

After the solid medium frame 21 and a liquid medium are inserted into their respective compartments within the container, a cap 23 is placed on the open mouth of the container. The cap is provided with a suitable resilient material 25 to mate with the upper most surface of the dividing wall 13 when the cap is secured in place. Means are provided for moving the cap into and away from a position where the resilient material 25 meets with the dividing wall 13. As shown in FIG. 1 the displacement means consists of screw threads 27 located in the outside sidewall of container 11 and the inside wall of the cap 23.

When the cap is secured into mating relationship with the dividing wall 13 the resilient material 25 is compressed and a liquid tight seal is formed between the first compartment 15 and the second compartment 17. Alternatively, an upper band of resilient material could be applied to the top of the dividing wall 13 and a solid filling material could replace the resilient material 25 to form the liquid tight seal.

It should be understood that the term "resilient material" as used herein refers to any material which may be sufficiently compressed by the cap moving means to form a liquid tight seal between the first compartment and the second compartment. Suitable resilient materials include, but are not limited to polyethylene, polypropylene, polyurethane, and nylon.

An inoculation port 29 is provided in the cap 11 for injecting a sample into the liquid medium 19. The inoculation port 29 comprises a septum 31 of suitable resilient material which is capable of being pierced by a needle or other injection means and which subsequently recloses upon extraction of the needle. Means, not shown, can be provided for permitting air to penetrate the first compartment 15 for aerobic incubation of the inserted sample. Such means would consist merely of a device with a hollow annular opening therethrough for penetrating the septum 31 to permit air to be admitted into the first compartment 15.

The container 11, cap 23 and solid medium tray 21 are formed from any suitable material, such as glass, plastic or metal. The container 11 is preferably formed from a transparent material, such as glass or plastic so that microbial growth on the solid medium can be seen from the outside. The container may be any suitable shape but is preferably cylindrical in shape for ease of manufacture.

During transport and inoculation the cap 23 is in mating relationship with the dividing wall 13. A sample is inserted through the septum 31 into the liquid medium 19. After a suitable incubation period, the cap 23 is moved upwardly so that a space is provided between the resilient material 25 and the dividing wall 13. The container is inverted to permit the liquid medium 19 to flow from the first compartment into the second compartment. Subsequent growth then occurs on the solid medium contained in the frame 21.

In accordance with the present invention an extremely simple device is provided for transporting and utilizing a liquid medium followed by subsequent inoculation of a solid medium with a sample incubated in the liquid medium. The culture bottle assembly of the present invention permits transportation of the liquid medium and the solid medium in separate compartments during transportation and provides easy means for transferring the precultured liquid medium into contact with the solid medium when desired.

What is claimed is:

1. A culture bottle assembly comprising:
    1. a container having a dividing wall which divides the container into a first compartment and a second compartment,
    2. a cap for said container,
    3. means for moving said cap axially with respect to said container,
    4. a resilient material which is compressed by said cap moving means to provide a liquid tight seal between said first compartment and said second compartment,
    5. a liquid nutrient medium in said first compartment, and
    6. a tray member having a congealed layer of solid medium in said second compartment.

2. A culture bottle assembly in accordance with claim 1 wherein said cap includes an aperture therethrough so that a liquid sample may be placed in said container.

3. A culture bottle assembly in accordance with claim 1 wherein said cap moving means include screw threads on the outside side wall of said container and mating screw threads on the inside side wall of said cap.

4. A culture bottle assembly in accordance with claim 1 wherein said resilient material is inside said cap.

5. A culture bottle assembly in accordance with claim 1 wherein said resilient material is located on top of said dividing wall.

6. A culture bottle assembly in accordance with claim 2 wherein said aperture has a needle piercable septum placed therein.

7. A culture bottle assembly in accordance with claim 1 wherein said tray member has a pyrimidal shape.

8. A culture bottle assembly comprising:
    a container having an interior with side walls, an exterior, and a dividing wall which divides the interior into a first compartment and second compartment,
    a cap for the container,
    cap moving means for moving the cap axially with respect to the container, and engaging said side walls
    a resilient material engaging said side walls for sealing the interior from the exterior, the resilient material being movable between first and second positions by the cap moving means such that in each position the interior is sealed from the exterior and the resilient material engages the dividing wall in the first position providing a liquid tight seal between the first and second compartments and fluid communication exists between the first and second compartments when the resilient material is in the second position.

* * * * *